(12) United States Patent
Vuckovic

(10) Patent No.: US 7,749,209 B1
(45) Date of Patent: Jul. 6, 2010

(54) COMPACT DISPOSABLE DIAPER CHANGING KIT PACKAGING

(76) Inventor: Miroslav Vuckovic, 9721 Keeler Ave., Skokie, IL (US) 60076

( * ) Notice: Subject to any disclaimer, the term of this patent is extended or adjusted under 35 U.S.C. 154(b) by 0 days.

(21) Appl. No.: 11/539,637

(22) Filed: Oct. 8, 2006

(51) Int. Cl.
*A61F 13/15* (2006.01)
*A61F 13/20* (2006.01)

(52) U.S. Cl. ............... 604/385.19; 604/385.06; 604/385.01

(58) Field of Classification Search ............ 604/385.01, 604/385.201, 385.06, 385.11, 385.19; 206/438–440
See application file for complete search history.

(56) References Cited

U.S. PATENT DOCUMENTS

| | | | |
|---|---|---|---|
| 4,702,378 A | 10/1987 | Finkel et al. | |
| 4,964,859 A | 10/1990 | Feldman | |
| 5,261,531 A | 11/1993 | Nieves | |
| 5,443,161 A | 8/1995 | Jonese | |
| 6,168,022 B1 * | 1/2001 | Ward et al. | 206/581 |
| 6,405,394 B1 * | 6/2002 | Rosenberg | 5/655 |
| 6,723,080 B1 | 4/2004 | Habib | |

* cited by examiner

*Primary Examiner*—Michele Kidwell

(57) ABSTRACT

A compact diaper changing kit packaging comprising a single sheet of flexible waterproof material enclosing a disposable diaper and pre-moistened wipes. The wipes are stored within a waterproof pouch formed by folding and sealing the enclosing sheet over upon itself. The enclosing sheet is wrapped around the diaper enclosing and protecting the diaper from contaminants. Method of use comprises unfolding the enclosing sheet to reveal disposable diaper and the waterproof pouch containing wipes. The unfolded enclosing sheet may be used as a clean changing surface. A dirty diaper and spent pre-moistened wipes may be stored away or disposed by wrapping them in the enclosing sheet.

3 Claims, 11 Drawing Sheets

COMPACT DISPOSABLE DIAPER CHANGING KIT PACKAGING

BACKGROUND

1. Field of the Invention

The present invention relates to a novel configuration of disposable diaper kit packaging that is easy to manufacture, transport, and apply.

2. Description of the Prior Art

Although parents typically have defined "changing stations" in their homes, they are often left in a lurch when out with their baby who may need a change: they may have a diaper, but no wipes; their wipes have dried out while sitting in their stroller or car for days; or they may not know what they have when leaving the house and thus "overpack" such items—unnecessarily increasing what they carry. Because of these needs, some have begun creating diaper changing "kits," but they still remain bulky, difficult to use, and complicated to manufacture.

More information relevant to attempts to address these problems can be found in following U.S. Patents.

U.S. Pat. No. 6,723,080 issued to Habib discloses an enclosure containing a set of individually packaged sanitary accessories including prepackaged moist baby wipes, prepackaged instant hand sanitizer, baby liner, and a disposable diaper.

U.S. Pat. No. 5,443,161 issued to Jonese discloses a baby changing kit with accessory items arranged within the enclosure to provide uniform and pliable surfaces for carrying and storage. The changing kit contains sanitary items for two complete diaper changes.

U.S. Pat. No. 5,261,531 issued to Nieves discloses a feminine hygiene package comprising a disposable container enclosing a dry wipe, an enclosed wet wipe, and a sanitary napkin.

U.S. Pat. No. 4,702,378 issued to Finkel discloses a disposable baby change kit comprising of a sheet of plastic film folded in such a way to provide a number of pockets receiving various hygiene accessories.

U.S. Pat. No. 4,964,859 issued to Feldman discloses a diaper with integral changing pad/disposable container wherein the changing pad is mounted on the outer surface of the diaper.

Nevertheless, each one of these references suffers from one or more of the following disadvantages. Most prior art designs are complex, utilizing numerous manufacturing elements and requiring complicated manufacturing processes, which in turn makes the product more expensive. Also, most present kits are bulky and therefore difficult to store and transport in large quantities. Furthermore, some kits are not easy to use as individual accessories are not easily manipulated while holding the infant in a safe manner.

For the foregoing reasons, there is a need for a diaper changing kit that is compact, easy to manufacture, and easy to use.

SUMMARY

The present invention is directed to a product that satisfies the need for diaper changing kit packaging that is compact, easy to manufacture, and easy to use.

The present invention uses a single sheet of flexible waterproof material to create a compact enclosure for a disposable diaper and pre-moistened wipes. The enclosure is easily and quickly unfastened and unfolded revealing one disposable diaper and a waterproof pouch containing one or more pre-moistened wipes. The unfolded enclosure can be used as a changing pad and may optionally have a water absorbent layer attached to its inwardly oriented face therefore increasing its effectiveness as a changing pad. The waterproof pouch is an integral part of the enclosure and is formed from the same body of enclosing sheet by folding it over upon itself and permanently sealing it. The access to pre-moistened wipes stored within the pouch is provided by tear-off tabs or a number of other opening means well known in the art concerning prepackaged sanitary tissues.

The advantages of the present invention are numerous. The present invention is easy and inexpensive to manufacture. The production process requires a limited number of manufacturing steps and manufacturing materials. The manufacturing process would comprise steps involving manipulation of a single sheet of flexible waterproof material. Required manufacturing materials comprise a disposable diaper, one or more pre-moistened wipes, and a sheet of flexible waterproof material.

Another advantage of the present invention is its compact form prior to use. A single disposable diaper and a small number of pre-moistened wipes, preferably three, are tightly enclosed within a flexible sheet of protective waterproof material. Consequently, the article is easy to dispense and transport either in bulk or individually.

Yet additional advantage of the present invention is its ease of use, which is especially important for caregivers while traveling. The kit can be easily unfastened and unfolded instantly providing a sanitary changing surface and revealing a disposable diaper. The waterproof pouch containing pre-moistened wipes is conveniently integrated within the changing surface and the access to enclosed wipes is easily obtained by unsealing the pouch. Most of disclosed steps may be accomplished with only one hand, which frees the caregiver to maintain safer changing environment for the infant.

These and other features, aspects, and advantages of the present invention will become better understood with reference to the following description and appended claims.

BRIEF DESCRIPTION OF THE SEVERAL VIEWS OF THE DRAWING

These and other features, aspects, and advantages of the present invention will become better understood with regard to the following description, appended claims, and accompanying drawings where:

DESCRIPTION

Figure 11:
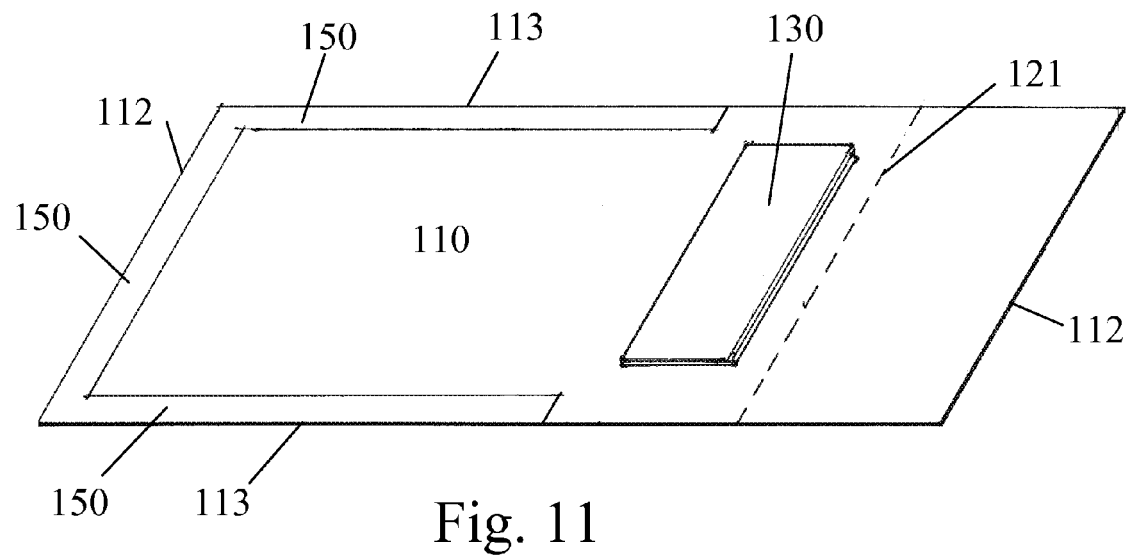
FIG. 11 is a perspective view of a sheet of waterproof material and pre-moistened wipes prior to assembling.
Figure 12A:
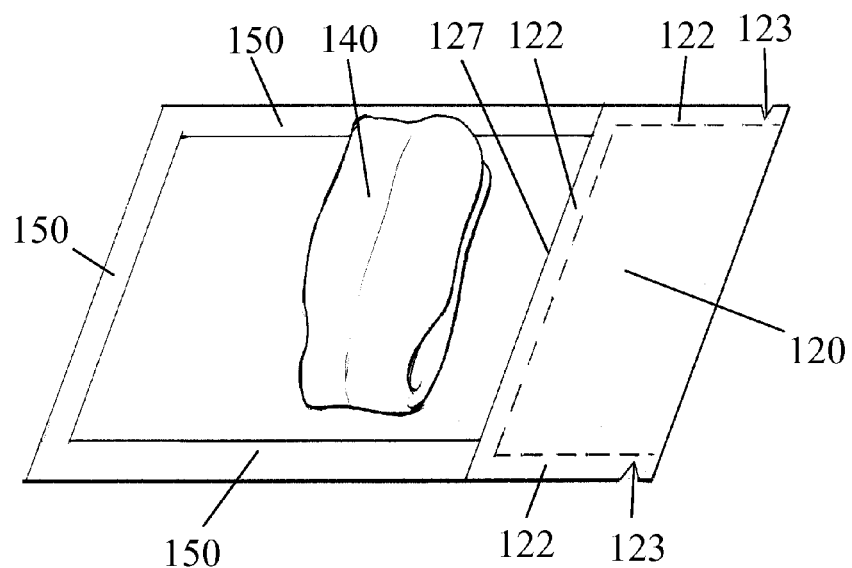
FIG. 12A is a perspective view of one invention embodiment shown in its unfastened and unfolded, ready-to-use, condition.
Figure 14A:
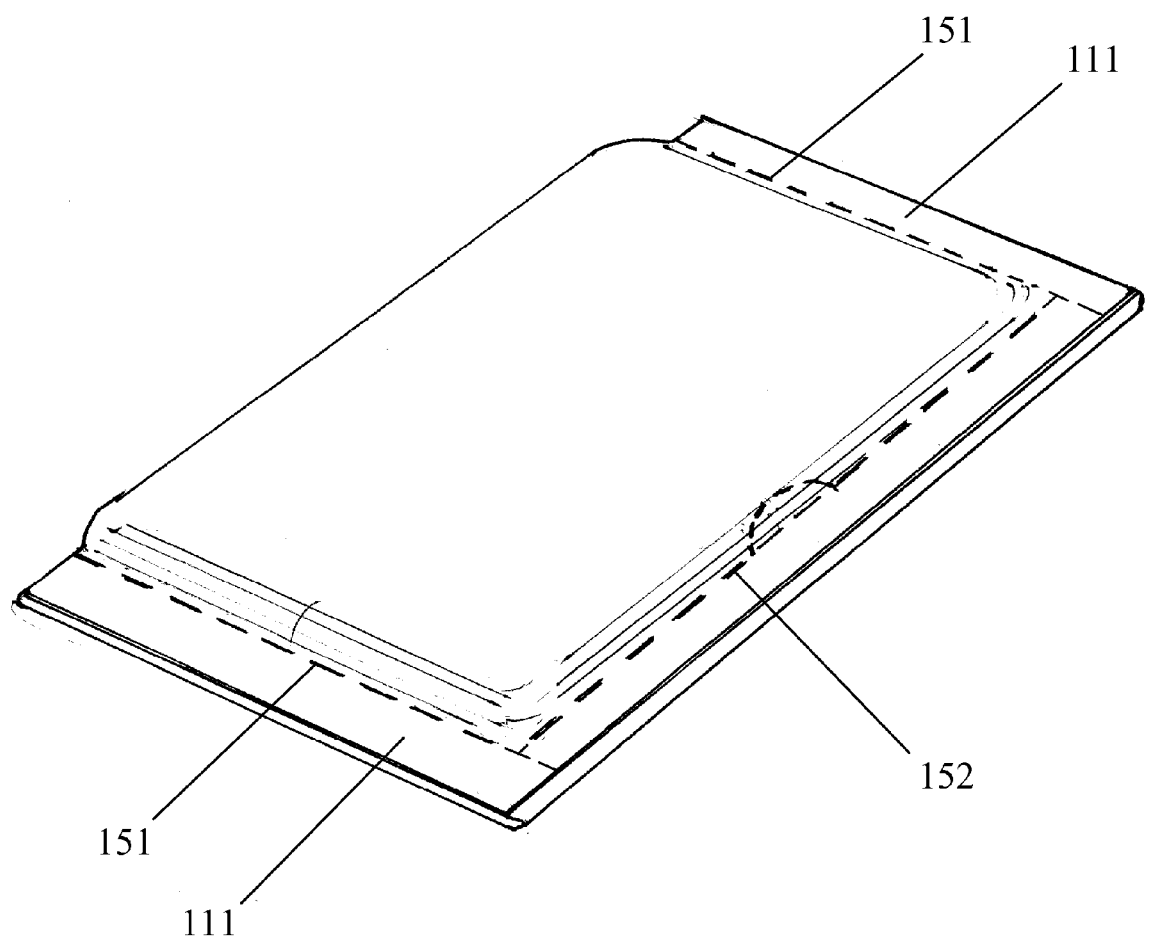
FIG. 14A is a perspective view of a closed configuration of one invention embodiment, showing lines along which the enclosure material may be weakened to provide easy opening of the kit.
Figure 14B:
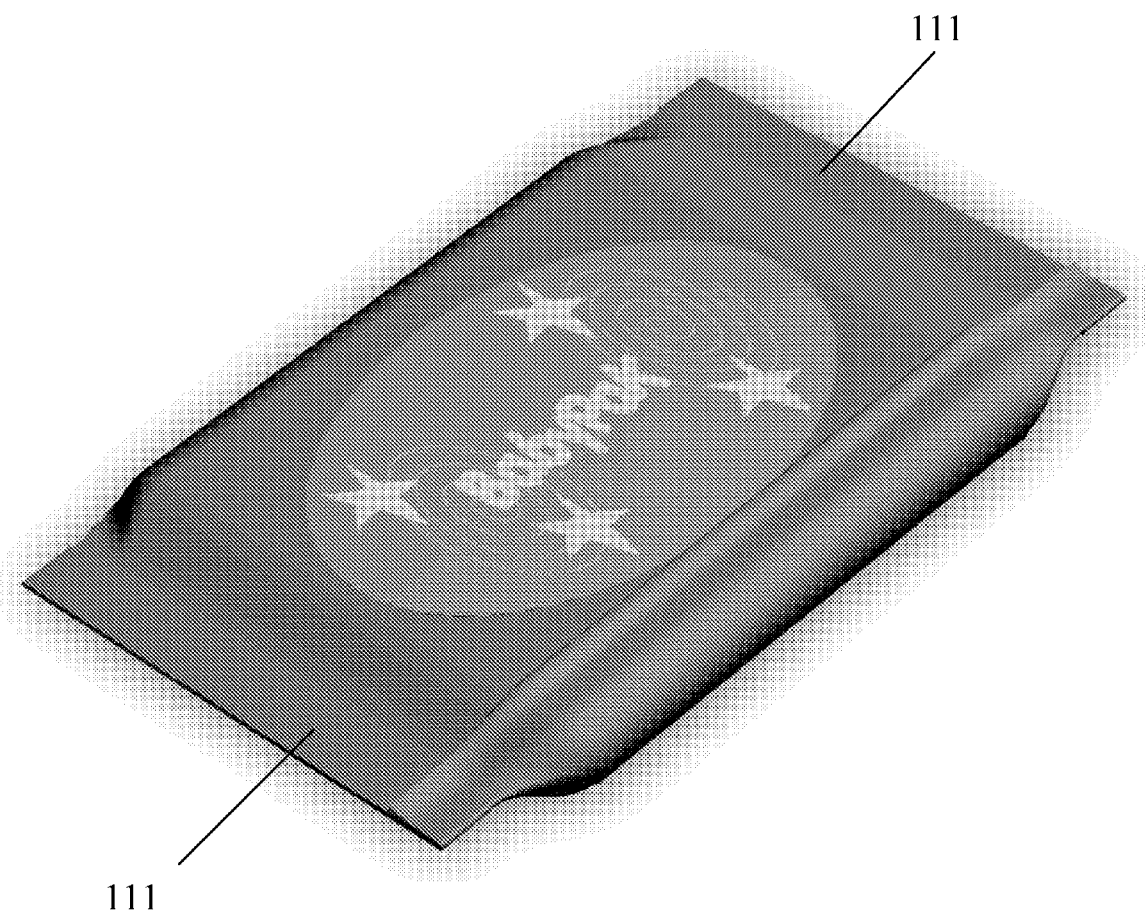
FIG. 14B is a perspective view of a closed configuration of one invention embodiment.
Figure 14C:
FIG. 14C is a top plan view of a closed configuration of one invention embodiment.
Figure 15:
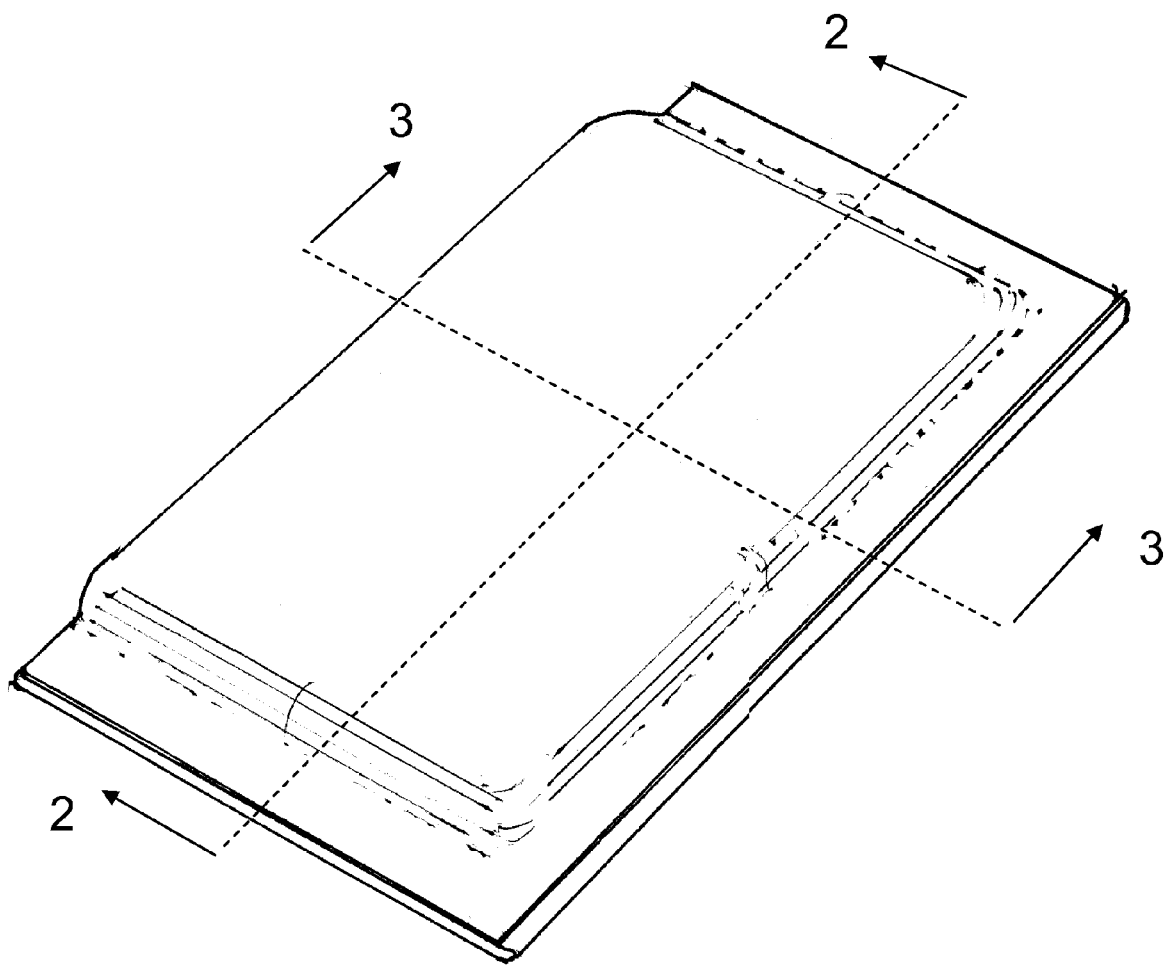
FIG. 15 is a perspective view of a closed configuration of one invention embodiment, showing cross-sectional view lines.
Figure 16:
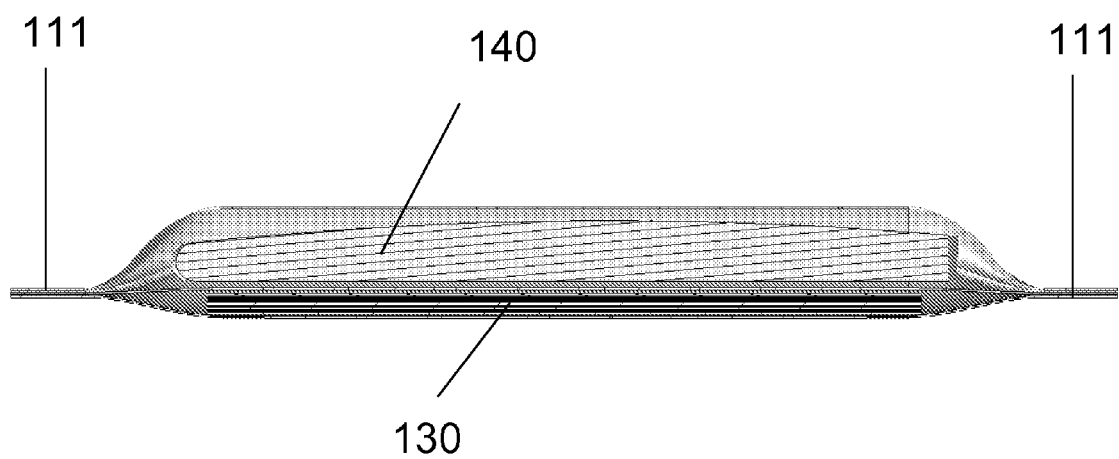
FIG. 16 is a vertical cross-sectional view of a closed configuration of one invention embodiment, such view being taken along line 2-2 in FIG. 15 and in the direction indicated.
Figure 17A:
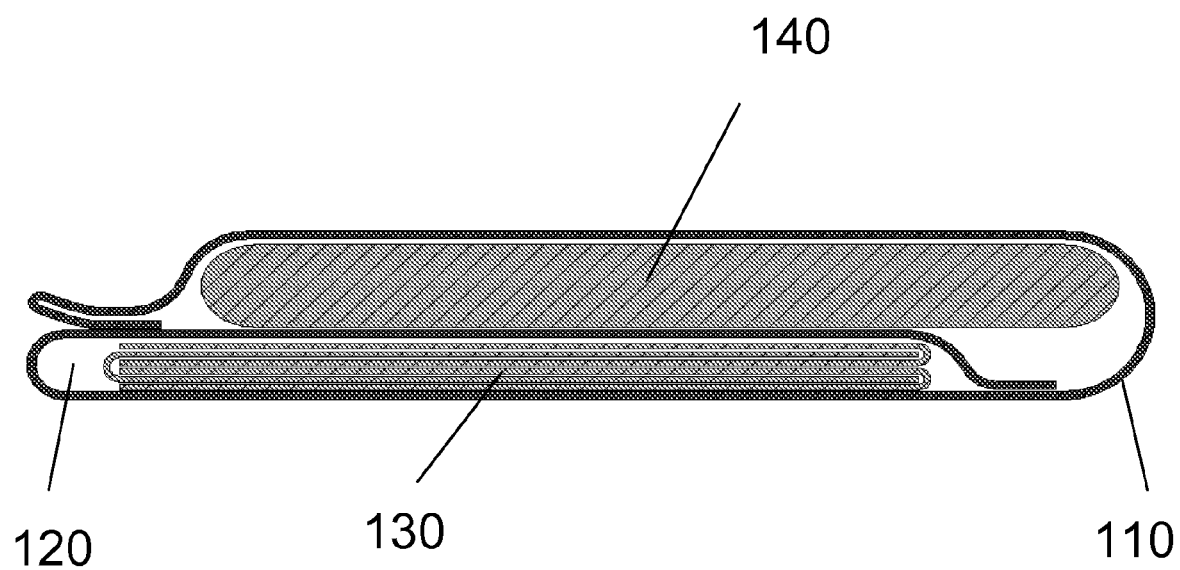
FIG. 17A is a vertical cross-sectional view of a closed configuration of one invention embodiment, such view being taken along line 3-3 in FIG. 15 and in the direction indicated.
Figure 17B:
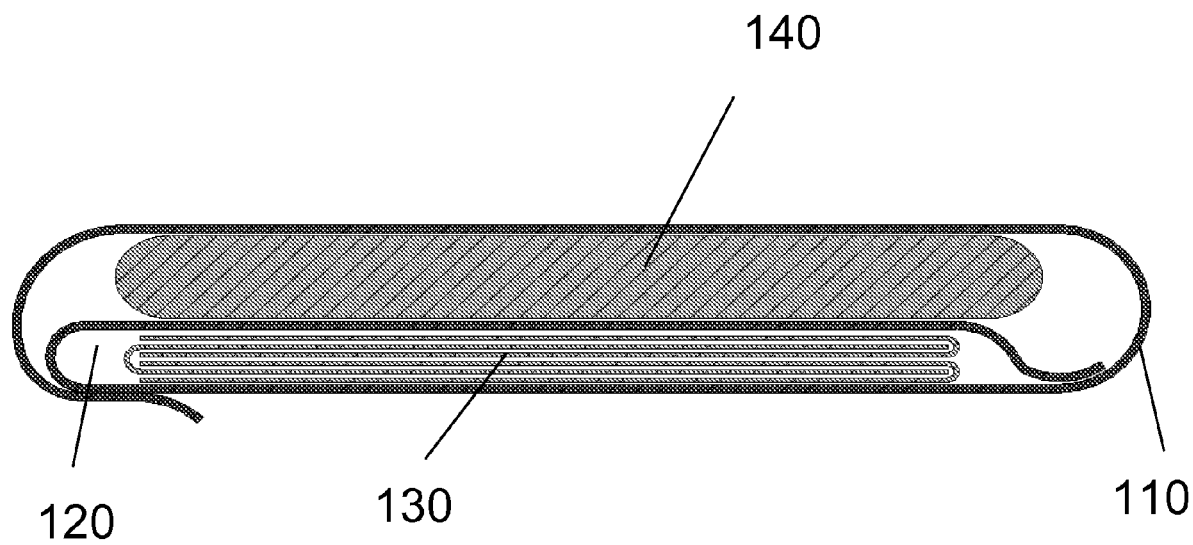
FIG. 17B is a vertical cross-sectional view of a closed configuration of one invention embodiment, such view being taken along line 3-3 in FIG. 15 and in the direction indicated.

FIG. 12A shows a diaper changing kit packaging in its opened and unfolded configuration. A sheet of flexible waterproof material 110, which is used as an enclosure for the entire kit, reveals a disposable diaper 140 and a waterproof pouch 120 containing one or more pre-moistened wipes 130. Drawings in FIG. 14A, FIG. 14B, FIG. 14C show the diaper changing kit packaging in various closed configurations.

The disposable diaper 140 is preferably a "snug-fit baby diaper" of conventional design and can be of different sizes for newborns, infants, toddlers, and even older children and adults. Still other diaper designs such as training pants and "pull-ups" could be used in the prepackaged diaper changing kit in accordance with the present invention.

The sheet of flexible waterproof material 110 provides numerous functions. Prior to opening, the sheet 110 serves as an enclosure for the entire kit, protecting the disposable diaper 140 and pre-moistened wipes 130 from external contamination. While the kit enclosure preferably provides a waterproof barrier to external contaminants, other embodiments of the present invention may not provide waterproof protection. Furthermore, the sheet 110 ensures the kit's compact form by tightly enveloping elements present in the kit. In its unfolded state, the sheet 110 may be used as a waterproof changing pad, providing a sanitary changing environment.

The material used for sheet 110 is flexible enough to sustain a number of foldings. The sheet 110 is folded upon itself along lateral line 121 forming pouch 120 for storing wipes 130. The sheet 110 is also wrapped around the diaper 140 completely enclosing the diaper 140.

The sheet 110 in its completely unfolded arrangement has a perimeter defined by lateral edges 112 and longitudinal edges 113. The lateral edges 112 have a length greater than the length of the enclosed diaper 140 or the length of the pre-packaged wipes 130, whichever is greater. The longitudinal edges 113 have sufficient length to allow the sheet 110 to fold around wipes 130, thereto creating an integrated waterproof pouch 120, and to completely wrap around the diaper 140. These minimal dimension requirements assure that the sheet 110 has sufficient length and width to perform as the kit enclosure, concealing and protecting the diaper 140 and wipes 130.

A number of different fastening methods may be utilized to fasten the sheet 110 to enclose the kit. For example, strips of adhesive 150 placed along inside edges of the sheet 110 would allow for tightly fastening the kit into its closed configuration. Preferably, the adhesive strips 150 are located substantially along two longitudinal edges 113 and substantially along a lateral edge 112 distal to the waterproof pouch 120, as shown in FIGS. 12A and 12C. Preferably the adhesive strips 150 would be resealable, allowing for refastening the kit when containing the used diaper and wipes. Yet other embodiments may utilize a permanent adhesive in the adhesive strips 150.

Another method to fasten the kit enclosure is to pressure-seal the strips 111, as shown in FIG. 14A, FIG. 14B, and FIG. 14C. The strips 111 are formed by folding the sheet 110 around the diaper 140 and sealing the folded longitudinal edges 113 into contact. The sealed area preferably stretches along the entire length of the strips 111.

To open the enclosures that utilize permanent adhesive strips 150 or pressure sealing of strips 111, the user may break open the fastening connection along edges 111. Preferably, the enclosing sheet 110 is weakened along lines 152 and 151 which are parallel to and closely separating the sealing edges 111 from the rest of the kit. The weakening lines 152 and 151 may be implemented as perforations of the enclosing sheet 110.

The materials used for the sheet 110 described above is well known in the art concerning liquid impermeable changing pads and in the art concerning sanitary napkin enclosures.

One or more, preferably three, pre-moistened wipes 130 are placed and sealed inside the waterproof pouch 120. The pouch 120 is created from the sheet 110 by folding the sheet 110 about line 121 over upon itself and over the wipes 130. The line 121 is substantially parallel to lateral edges 112 of the sheet 110. The sheet 110 may be folded either upon its inwardly or outwardly oriented face. The edges 122 of the pouch 120 are sealed creating a liquid impermeable container for the enclosed wipes 130.

The wipes 130 are placed within the pouch 120 preferably having their longer axis parallel to the folding line 121. The folded portion of the sheet 110 has width dimension sufficiently large to allow for the flat positioning of wipes 130 within the pouch 120 and for sealing the pouch 120 along pouch edges 122.

Access to wipes 130 may be provided in a number of ways such as tear-off tabs 123, pull string 124, peal-strip 125, or by unsealing the adhesive strips along pouch edges 122.

Figure 12B:
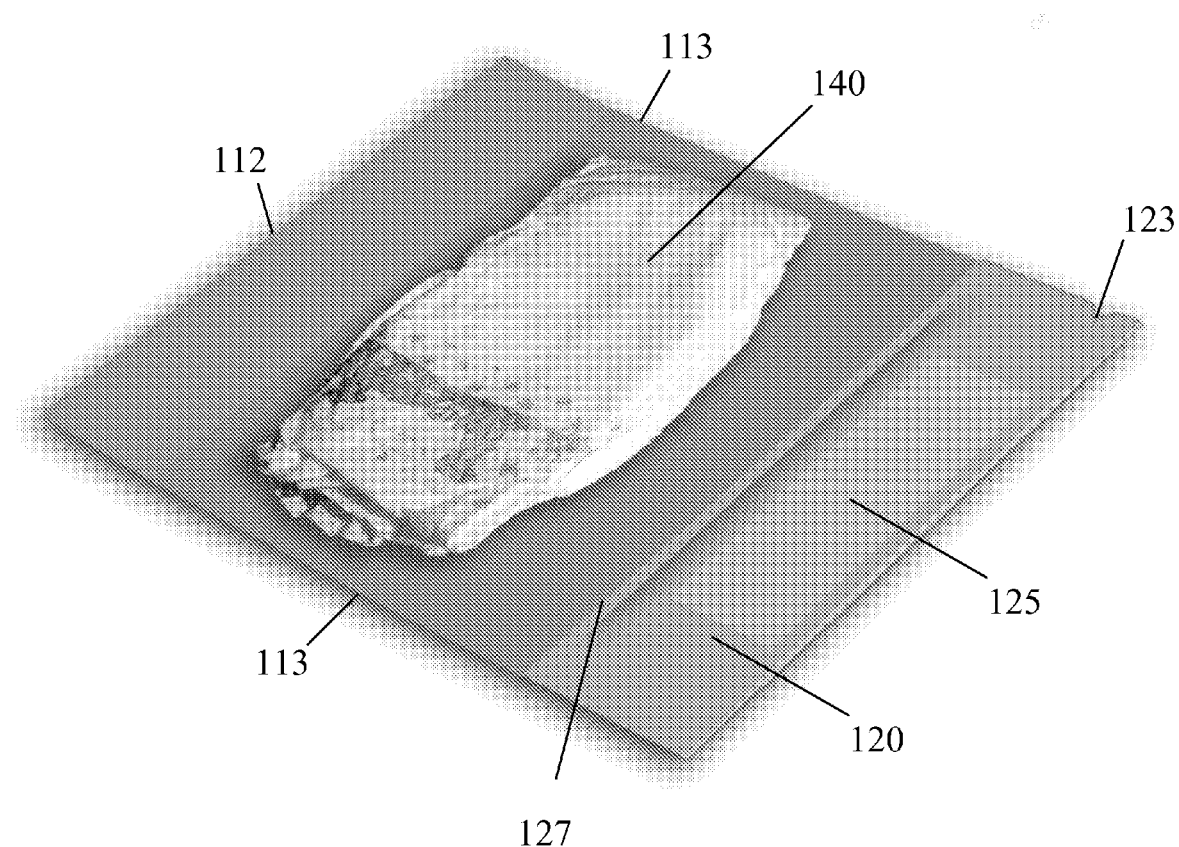
FIG. 12B is a perspective view of one invention embodiment shown in its unfastened and unfolded, ready-to-use, condition.
Figure 12C:
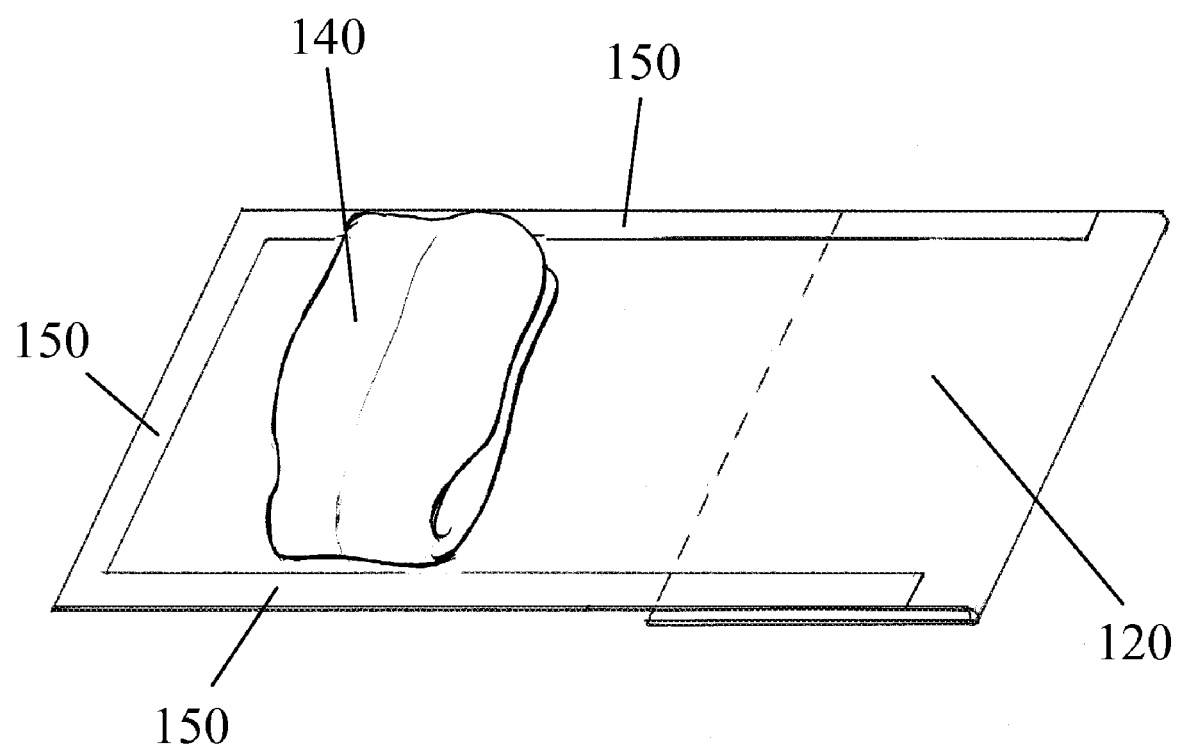
FIG. 12C is a perspective view of one invention embodiment shown in its unfastened and unfolded, ready-to-use, condition.

As shown in FIG. 12A and FIG. 12B, one or more tear-off tabs 123 may be located along the edges of the pouch 120, allowing for ripping an opening on the pouch 120 to create access to wipes 130.

Figure 13A:
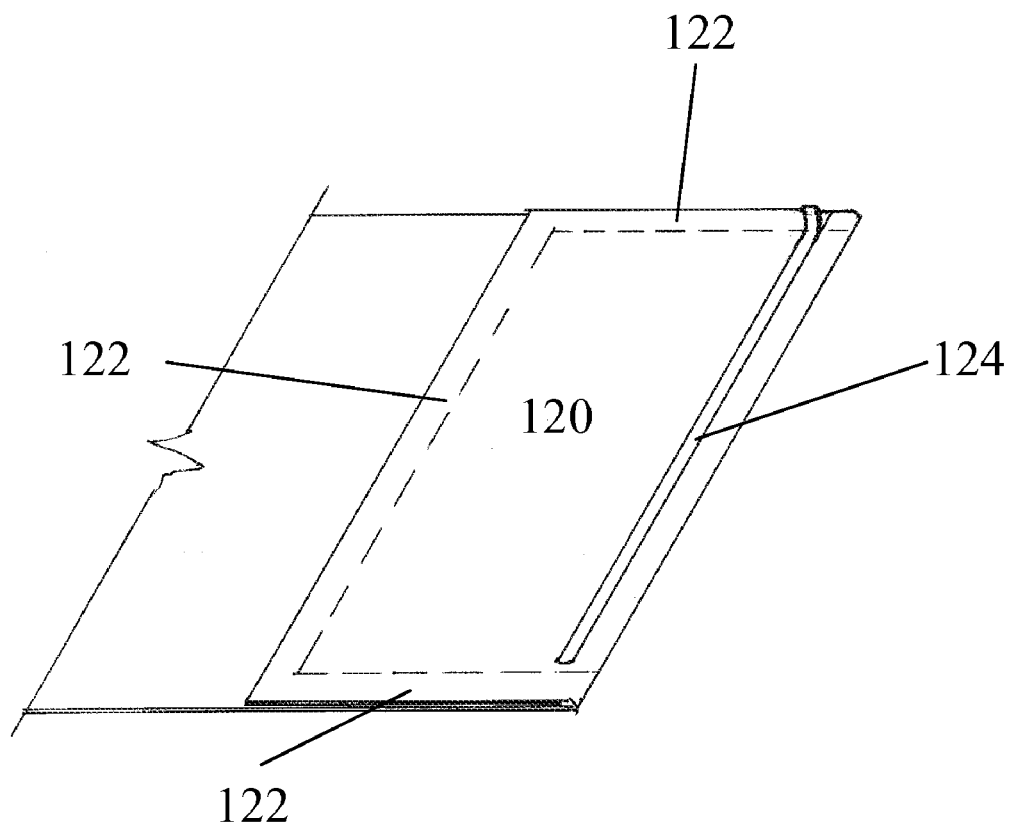
FIG. 13A is a perspective view of one embodiment of the waterproof pouch with pre-moistened wipes, the embodiment having a pull-string opening configuration.

One or more pull-strings 124 may be used to provide access to wipes 130. As shown in FIG. 13A, a pull-string 124 is in connection with the pouch 120 causing the ripping of the pouch 120 when the pull-string 124 is forcibly removed. Preferably, the pull-string 124 is inserted along the folding line 121 during the assembly of the pouch 120.

Figure 13B:
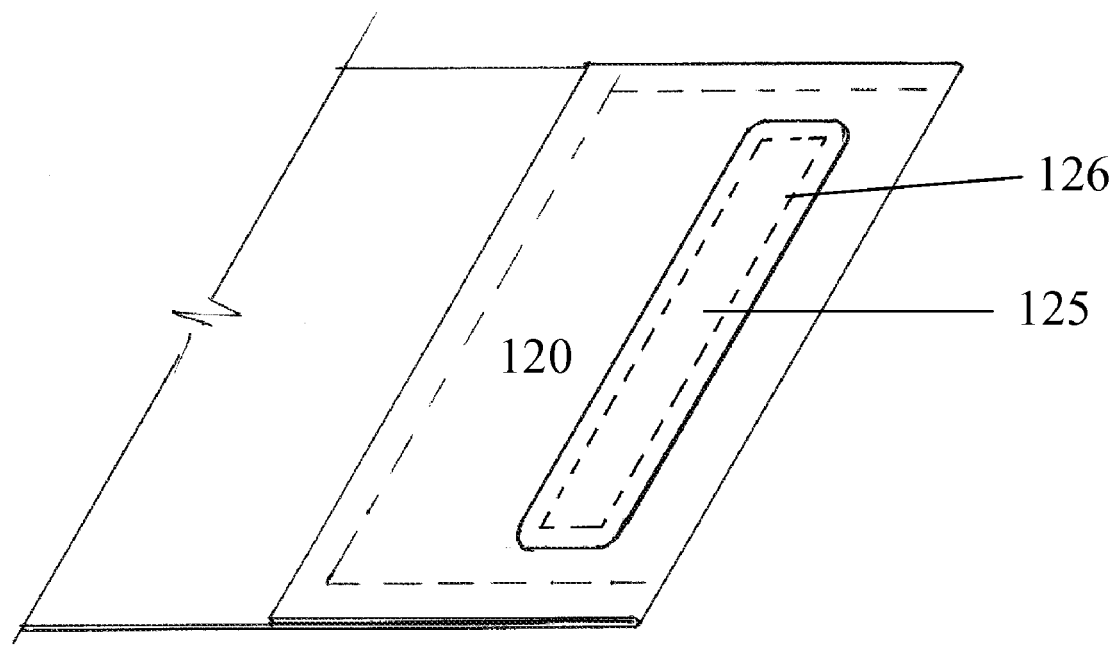
FIG. 13B is a perspective view of one embodiment of the waterproof pouch with pre-moistened wipes, the embodiment having a peal-strip opening configuration.

One or more peal strips 125 may be used to access wipes 130. As shown in FIG. 13B, a peal-strip 125 is affixed over an opening 126 in the pouch wall. The access to wipes 130 is achieved by removing the peal-strip 125. Preferably, the peal-strip is affixed to the pouch 120 using adhesive, but other methods, such as a pressure seal, may be used.

Another embodiment of the invention may utilize strips of non-permanent adhesive located along the pouch edges 122. To access the wipes 130, the user would pull the pouch wall thereby unsealing the adhesive along the pouch edges 122.

All of the aforementioned opening techniques are widely utilized or at least well known in the art of packaging sanitary and other consumer articles.

At least one, and more preferably three, pre-moistened wipes 130 are stored inside the waterproof pouch 120. Pre-moistened wipes 130 preferably have a rectangular configuration in the range of approximately four to eight inches in height and in the range of approximately six to twelve inches in width and most preferably are approximately seven inches in height by eight inches in width. The wipes 130 are folded to form a rectangular shape preferably having approximately seven inches in height by approximately eight inches in width.

The sheet 110 has opposed faces, with the inwardly oriented face being in proximity to the diaper 140. Optionally, a water absorbent layer may be attached to the inwardly oriented face of the sheet 110. Materials and processes for making and attaching the water absorbent layer include those that are known concerning the disposable diaper and disposable bed pad arts.

The present invention discloses a compact disposable diaper changing kit that is easily used by a caregiver. The caregiver can easily open and unfold the kit to reveal one disposable diaper 140 and a sealed waterproof pouch 120 containing one or more pre-moistened wipes 130. The unfolded sheet 110 may be used as a changing pad to keep the baby clean as well as to prevent the changing surface from being soiled. The access to wipes 130 is easily gained by creating an opening in the pouch 120. After a diaper change, the soiled diaper and wipes can be wrapped in the same sheet 110 for sanitary disposal.

The present invention has many advantages, including ease of manufacturing, ease of use, and its compact and aesthetically appealing design.

As shown in FIGS. 14A, 14B and 14C, the closed kit is compact as it tightly encloses a small number of diaper changing accessories. The flexible sheet 110 performs a number of functions such as providing an enclosure for the entire kit, providing a watertight enclosure for pre-moistened wipes 120, and serving as a changing pad when unfolded.

Furthermore, the manufacturing process is straightforward and easily streamlined since it mostly involves a manipulation of a single sheet of material. For instance, a small number of manufacturing steps performed on the sheet 110 may comprise placing pre-moistened wipes 120 on the sheet 110, folding and pressure sealing the pouch 120, optionally cutting out a tear-off tab 123, placing one disposable diaper 140 on the sheet 110, optionally applying strips of adhesive, and finally folding and fastening the kit.

In addition to other advantages, the present invention is extremely easy to use which is especially important in places that necessitate additional care to keep the infant safe while changing the diaper. The closed kit is easily unfastened and unfolded. After placing the infant on an unfolded sheet 110, the user would access the pre-moistened wipes 130 by opening the pouch 120. After the diaper change, the sheet 110 may be used as a waste container for the storage of used wipes and soiled diapers. Similarly, this invention can be used by adults with incontinence problem.

This invention does not require that all the advantageous features and all the advantages need to be incorporated into every embodiment of the invention.

Although the present invention has been described in considerable detail with reference to certain preferred versions thereof, other versions are possible. Therefore, the spirit and scope of the appended claims should not be limited to the description of the preferred versions contained herein.

What is claimed is:

1. A diaper kit packaging consisting of:
a disposable diaper;
one or more pre-moistened wipes;
a sheet of flexible waterproof material, wherein the sheet is wrapped around the diaper and fastened upon itself providing a protective enclosure for the diaper, and wherein the sheet in unfolded configuration is capable of performing as a changing pad;
a waterproof pouch for storing the wipes, wherein the pouch is made by folding a section of the sheet of flexible waterproof material about a lateral line of the sheet and by sealing the folded section upon the sheet creating a liquid impermeable container for the wipes, and wherein the pouch has one or more tear-off tabs located on edges of the waterproof pouch for opening the pouch; and
strips of adhesive located on an inwardly oriented face of the single sheet of flexible waterproof material, wherein the strips of adhesive are located substantially along longitudinal edges of the sheet and substantially along an edge of the sheet distal to the waterproof pouch.

2. A diaper kit packaging consisting of:
a disposable diaper;
one or more pre-moistened wipes;
a sheet of flexible waterproof material, wherein the sheet is wrapped around the diaper and fastened upon itself providing a protective enclosure for the diaper, and wherein the sheet in unfolded configuration is capable of performing as a changing pad;
a waterproof pouch for storing the wipes, wherein the pouch is made by folding a section of the sheet of flexible waterproof material about a lateral line of the sheet and by sealing the folded section upon the sheet creating a liquid impermeable container for the wipes, and wherein the pouch has an opening within a pouch wall covered with a removable peel strip; and
strips of adhesive located on an inwardly oriented face of the single sheet of flexible waterproof material, wherein the strips of adhesive are located substantially along longitudinal edges of the sheet and substantially along an edge of the sheet distal to the waterproof pouch.

3. A diaper kit packaging consisting of:
a disposable diaper;
one or more pre-moistened wipes;
a sheet of flexible waterproof material, wherein the sheet is wrapped around the diaper and fastened upon itself providing a protective enclosure for the diaper, and wherein the sheet in unfolded configuration is capable of performing as a changing pad;
a waterproof pouch for storing the wipes, wherein the pouch is made by folding a section of the sheet of flexible waterproof material about a lateral line of the sheet and by sealing the folded section upon the sheet creating a liquid impermeable container for the wipes, and wherein the pouch has a pull-string for ripping open the pouch; and
strips of adhesive located on an inwardly oriented face of the single sheet of flexible waterproof material, wherein the strips of adhesive are located substantially along longitudinal edges of the sheet and substantially along an edge of the sheet distal to the waterproof pouch.

* * * * *